(12) United States Patent
Sadoddin et al.

(10) Patent No.: US 10,878,341 B2
(45) Date of Patent: Dec. 29, 2020

(54) MINING AND VISUALIZING ASSOCIATIONS OF CONCEPTS ON A LARGE-SCALE UNSTRUCTURED DATA

(71) Applicant: FAIR ISAAC CORPORATION, Roseville, MN (US)

(72) Inventors: Reza Sadoddin, San Jose, CA (US); Osvaldo A. Driollet, San Diego, CA (US)

(73) Assignee: Fair Isaac Corporation, Roseville, MN (US)

( * ) Notice: Subject to any disclaimer, the term of this patent is extended or adjusted under 35 U.S.C. 154(b) by 955 days.

(21) Appl. No.: 15/464,254

(22) Filed: Mar. 20, 2017

(65) Prior Publication Data
US 2018/0039909 A1  Feb. 8, 2018

Related U.S. Application Data

(60) Provisional application No. 62/310,584, filed on Mar. 18, 2016.

(51) Int. Cl.
| | |
|---|---|
| *G06N 20/00* | (2019.01) |
| *G06K 9/62* | (2006.01) |
| *G06F 16/35* | (2019.01) |
| *G06F 16/33* | (2019.01) |
| *G16B 40/00* | (2019.01) |
| *G16B 50/00* | (2019.01) |
| *G06N 5/02* | (2006.01) |
| *G06K 9/00* | (2006.01) |

(52) U.S. Cl.
CPC ......... *G06N 20/00* (2019.01); *G06F 16/3331* (2019.01); *G06F 16/35* (2019.01); *G06K 9/00* (2013.01); *G06K 9/623* (2013.01); *G06K 9/6224* (2013.01); *G06N 5/022* (2013.01); *G16B 40/00* (2019.02); *G16B 50/00* (2019.02)

(58) Field of Classification Search
None
See application file for complete search history.

(56) References Cited

U.S. PATENT DOCUMENTS

| 2007/0124291 A1* | 5/2007 | Hassan ................... G06F 16/34 |
| 2008/0154926 A1* | 6/2008 | Newman ............... G06Q 10/107 |
| 2009/0319518 A1* | 12/2009 | Koudas ................. G06F 16/338 |

(Continued)

OTHER PUBLICATIONS

Sadoddin et al., Mining and Visualizing Associations of Concepts on a Large-scale Unstructured Data, 2016 IEEE Second International Conference on Big Data Computing Service and Applications, pp. 216-224 (Year: 2016).*

(Continued)

*Primary Examiner* — Alan Chen
(74) *Attorney, Agent, or Firm* — Mintz Levin Cohn Ferris Glovsky and Popeo, P.C.; Mike Van Loy, Esq.; F. Jason Far-hadian, Esq.

(57) ABSTRACT

A problem of finding unknown associations between 'concepts' in a given text corpus is addressed. A new framework for computing and visualizing the association between concepts using the generic association measures and the public knowledge available in data sources such as Wikipedia. Indirect association analysis extends the utility of the proposed framework to a broader class of association mining applications including the interesting area of new hypothesis generation.

12 Claims, 9 Drawing Sheets

(56) References Cited

U.S. PATENT DOCUMENTS

| | | | | |
|---|---|---|---|---|
| 2012/0278321 | A1* | 11/2012 | Traub | G06F 16/3331 707/736 |
| 2013/0196877 | A1* | 8/2013 | Banerjee | G16B 25/00 506/9 |
| 2014/0222506 | A1* | 8/2014 | Frazer | G06Q 30/02 705/7.29 |
| 2017/0220674 | A1* | 8/2017 | Malik | G06N 20/00 |
| 2017/0221240 | A1* | 8/2017 | Stetson | G06F 16/9024 |
| 2018/0082183 | A1* | 3/2018 | Hertz | G06K 9/6259 |
| 2020/0019555 | A1* | 1/2020 | Ramani | G06Q 10/00 |

OTHER PUBLICATIONS

Disgenet Database, http://www.disgenet.org, Accessed May 15, 2015. Retrieved from Internet Archive,https://web.archive.org/web/20150827203324/http://www.disgenet.org/web/DisGeNET/menu;jsessionid=rucacz1a4h5clyi5b9urswjg. Accessed on Jun. 28, 2017. 5 pages.

Medicinenet, http://www.medicinenet.com/, Accessed Nov. 19, 2015. Retrieved from Internet Archive, https://web.archive.org/web/20151119022402/http://www.medicinenet.com/script/main/hp.asp. Accessed on Jun. 28, 2017. 3 pages.

Srinivasan, P. "Text Mining: Generating Hypotheses From Medline." *Journal of the American Society for Information Science and Technology,* vol. 55 No. 5, (2004), pp. 396-413.

Swanson, D. R. "Fish Oil, Raynaud's Syndrome, and Undiscovered Public Knowledge," *Perspectives in Biology and Medicine,* vol. 30, No. 1, (1986), pp. 7-18.

Swanson, D. R. "Two Medical Literatures That Are Logically But Not BibliographicallyConnected." *Journal of the American Society for Information Science,* vol. 38, No. 4, (1987), pp. 228-233.

Thanopoulos, A., et. al. "Comparative Evaluation of Collocation Extraction Metrics." *Proceedings of the Third International Conference on Language Resources and Evaluation* (LREC-2002), (May 2002), pp. 620-625.

Tsuruoka, Y., et. al. "Discovering and Visualizing Indirect Associations Between Biomedical Concepts," *Bioinformatics,* vol. 27, No. 13 (2011), pp. i111-i119.

Wren, J. D. "Extending the Mutual Information Measure to Rank Inferred Literature Relationships." *BMC Bioinformatics,* vol. 5, (2004), p. 145. (13 pages). [Online]. Available: http://dblp.uni-trier.de/db/journals/bmcbi/bmcbi5.htmlWren04.

Yetisgen-Yildiz, M. and W. Pratt. "A New Evaluation Methodology for Literature-Based Discovery Systems." *Journal of Biomedical Informatics,* vol. 42, No. 4, (2009), pp. 633-643.

\* cited by examiner

MINING AND VISUALIZING ASSOCIATIONS OF CONCEPTS ON A LARGE-SCALE UNSTRUCTURED DATA

TECHNICAL FIELD

The subject matter described herein relates to systems and methods for mining associations of concepts gathered from large-scale unstructured data, and providing visualizations of those mined associations of concepts.

BACKGROUND

Finding associations between concepts have applications in different domains, ranging from Medicine to Material sciences. The associations between different types of diseases, genes, symptoms, treatments, and drugs can be used to understand the functional relationships between medical concepts, and potentially come up with new preventive care, diagnostic methods, or cures for diseases. Extending the association analysis to 'indirect' association mining enables us to find more subtle relationship s between concepts and propose new hypotheses for further research. This is of great benefit to researchers to focus on hypotheses with stronger evidences.

In addition to providing valuable insight as described above, the extracted associations between concepts can be exploited in higher level analytics. This includes the data mining techniques used for association rule mining (e.g. to characterize the associations between a group of genes to absence or presence of an enzyme), the predictive modeling techniques aimed an predicting a 'target' variable based on the features extracted from the concepts (e.g. to predict the probability of hazardness of under-development hand-soaps on body skin based on the materials used in the product and their associations with skin tissues, cell layer, and nerves), or clustering methods used to find similar concepts to each other (e.g. to estimate the side effects of new drugs based on their similarity to other drugs).

The unstructured data is widespread and available at no or minimum cost in the World Wide Web. An example source of information is Wikipedia which covers a broad spectrum of sciences in the format of text. This is just a tiny amount of data compared to many other sources of data and many other domain-specific public databases available. Statistical correlation techniques, such as Point-Wise Mutual Information can be used to measure the association between concepts in a text corpus, by quantifying the co-occurrence of these concepts with respect to their individual appearances.

Even though the unstructured data is widespread and can be tapped into for extracting valuable information and insights, automatic mining of such huge amount of data can become challenging when processing large-scale unstructured data sources. The naive pair-wise correlation measuring of concepts between concepts becomes computationally inefficient due to its quadratic time complexity.

One prior technique is known as literature-based discovery. Many literature-based discovery systems have been developed to find new connections between biomedical terms that could lead to new directions in research. The proposed approach was based on a combination of citation analysis and manual review, in which the potential novelty is discovered by citation analysis, and the manual review step is used to identify plausible new connections across disjoint literature works. For instance, this approach was used to hypothesize the role of fish oil in clinical treatment of Raynaud's disease, combining different pieces of information from the literature, and the hypothesis was later confirmed with experimental evidence.

Tsuruoka et al. FACTA+, discloses a real-time text mining system for finding indirect associations between biomedical concepts from MEDLINE abstracts. The system is described as being capable of producing ranked lists of important biomedical concepts which are considered relevant to the query according to their co-occurrence statistics. The proposed system can also been used as a search engine to link biomolecular pathways to textual evidence. The main idea behind FACTA is to find indirect associations between biomedical terms through a group of intermediate terms. A new association score for evaluating the indirect relationship between terms is proposed, which depends on both the reliability and novelty of association.

What is needed is a computer-implemented way to find associations in a large-scale dictionary of concepts and corpus.

SUMMARY

This document describes systems and methods for mining associations of concepts gathered from large-scale unstructured data, and providing visualizations of those mined associations of concepts. Generally, the problem addressed can be described as follows: given a large-scale dictionary of concepts, and a text corpus, pairs of concepts which are "associated" to each other can be determined. The association can be interpreted in a particular domain of study. For instance, a disease is associated with its symptoms, or a drug is associated with the disease(s) it can cure or the side effects resulted by using the drug. The text corpus given as the reference knowledge contains information about the concepts contained in the input dictionary in the format of text. It is then determined whether two given concepts are associated.

Implementations of the current subject matter can include, but are not limited to, systems and methods consistent with implementations described herein, as well as articles that comprise a tangibly embodied machine-readable medium operable to cause one or more machines (e.g., computers, etc.) to result in operations described herein. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an enterprise resource software system or other business software solution or architecture, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

This document describes systems and methods for mining associations of concepts gathered from large-scale unstructured data, and providing visualizations of those mined associations of concepts. Given a large-scale dictionary of concepts, and a text corpus, pairs of concepts that are "associated" to each other can be determined. The association can be interpreted in a particular domain of study. The text corpus given as the reference knowledge contains information about the concepts contained in the input dictionary in the format of text. It is then determined whether two given concepts are associated.

Figure 1:
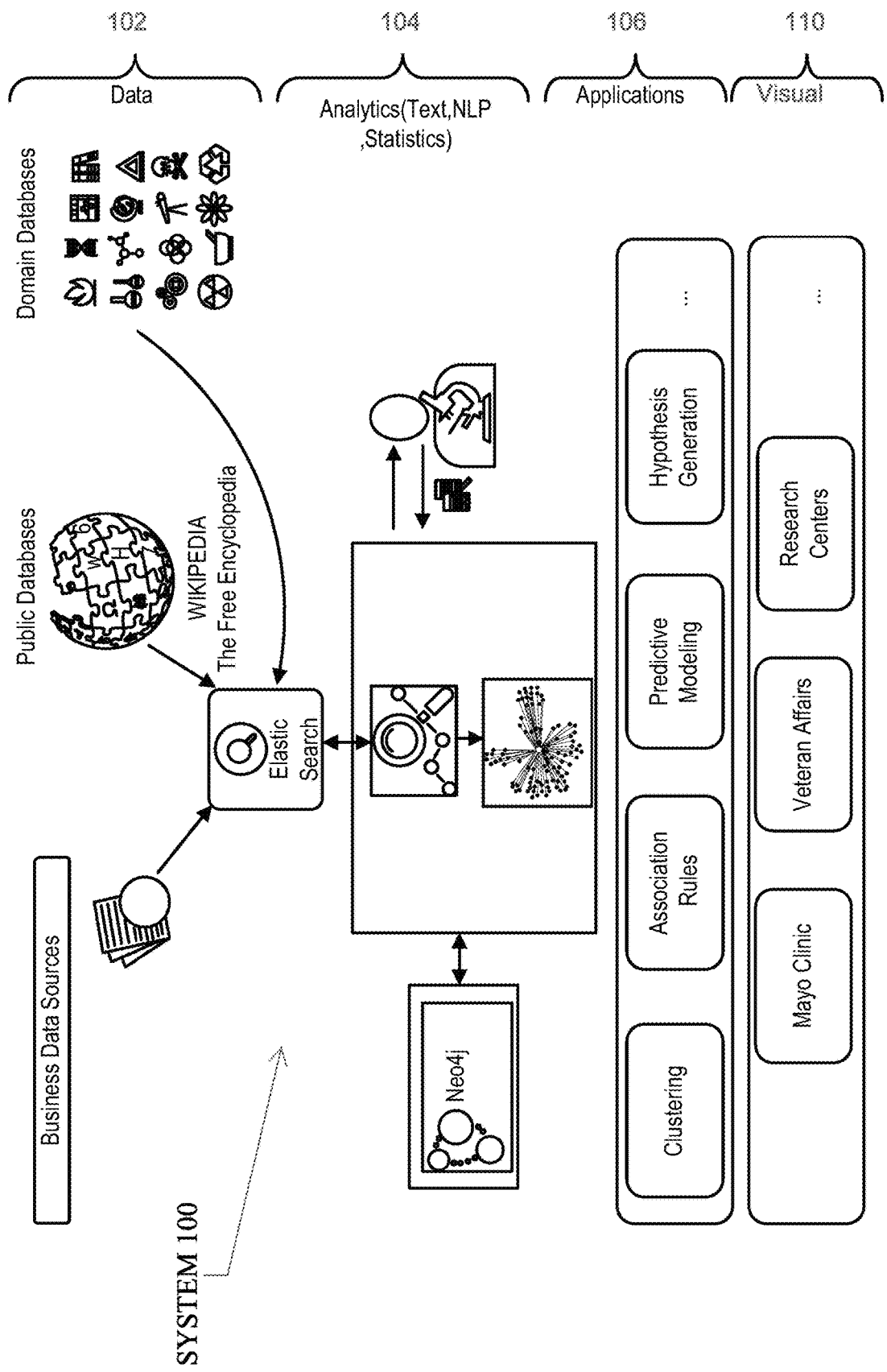
FIG. 1 illustrates a general outline of the presently described framework having one or more features consistent with the present disclosure.

FIG. 1 illustrates a system 100. A data layer 102 includes one or more data sources, including the business data sources, public databases, and domain-specific databases. The main input to the system 100 is defined by the text documents to be processed, as well as by the dictionary of concepts to be investigated. Public and domain-specific databases can be used as the text corpus from which the associations between concepts can be computed. A full text search engine such as Elasticsearch can be used as the main datastore for document indexing, as well as for supporting the primary query engine for computing the statistics of concepts and their associations.

An analytics layer 104 includes a primary computation engine and visualization dashboard of the framework, where the required statistics are calculated for all the terms in the dictionary, and pair-wise statistics (e.g. co-occurrence of terms) are just calculated for pairs of terms which are likely to be associated. The results of association analysis between concepts are shown using a graph database management system's visualization capabilities, such as Neo4J, where concepts are shown as 'nodes' in the graphs and associations are shown as 'edges' of the graphs. Neo4J is a graph database which not only provides a user-friendly interface for visualizing the associations, but also can be utilized for a more thorough analysis by means of its SQL-inspired query language Cypher.

An applications layer 106 provides higher-level analytics and insight discovery derived from the extracted associations using machine learning, data mining, and statistical analysis techniques. The associations between the concepts can be 1) modeled as a graph and clustered (e.g. using the community detection algorithms provided by the Neo4J database), 2) used to find new associations rules in the data, 3) employed either as predictive features or new target variables in predictive modeling scenarios, or 4) used to generate hypothesis for research in life sciences. Mining the associations between concepts in a large dictionary using different data sources can use several statistical correlation measures in finding the associations between concepts based on their co-occurrence in a text corpus. Experimental results show that the proposed associations measure outperforms the standard association measure based on point-wise mutual information.

A visualization layer 110 of the framework is developed on top of the highly scalable graph database. Using visualization capabilities of the graph database, the extracted associations in a large graph can be investigated in different levels of granularity. This basic insight can be enriched using features such as the Neo4J such as "betweenness centrality," "community detection," and ad-hoc query processing for thorough analysis of concepts and their associations.

Finding Direct Associations

An important element of computing direct associations between two concepts is the statistics related to the number of co-occurrences of these concepts within a text corpus. The number of co-occurrences of these concepts should be evaluated in a text "building block," which represents the "unit" of unstructured data on which the individual statistics are computed. In a text corpus, the units of analysis can be documents, paragraphs, sentences, or a text window of a specific length, where the length parameter defines the number of words in a text unit. The units can be defined as windows of any specific length, since sentences, paragraphs, pages, and even chapters could be the coarse building blocks used for measuring the associations between concepts. With this setting, a text window gives us the flexibility to define the granularity of co-occurrences of concepts.

The following four statistical correlation measures can be used for computing the associations between a pair of concepts:

Point-wise Mutual Information (PMI). The point-wise mutual information (PMI) is a widely used measure of association. It quantifies the dependencies between variables, including the co-occurring terms in text. The PMI score of two terms m and n can be defined as follows:

$$PMI(m, n) = \log\left(\frac{P_{mn}}{P_m P_n}\right) \quad (1)$$

where $P_{mn}$ is the joint probability of terms m and n co-occurring together in a same text window, and $P_m$ and $P_n$ represents the probabilities of occurrence of terms m and n, respectively.

Count Pointwise Mutual Information (PMIcount). The point-wise mutual information has a bias toward overestimating the correlation measure for "rare" events. The intuition behind this fact is that the join probability of two events is at most equal to the individual probabilities (e.g. in case two terms $W_1$ and $W_2$ are perfectly dependent, $P(W_1)=P(W_2)=P(W_1 \ W_2)=f$). So the core PMI formula will be reduced to $$\frac{f}{f^2},$$

in which case f will not grow as fast as $f^2$.

The count Pointwise mutual information (PMIcount) is defined as follows:

$$PMIcount(m,n) = near\_count(m,n) \times PMI \qquad (2)$$

where near_count(m, n) is referred to the number of times the terms m and n co-occur with each other. By using this modification, PMI count also takes into account the frequency of co-occurrences of two events, avoids the problem of bias towards rare events.

Z-Score. The Z-score measure focuses on term probability distributions to mine concept correlations in text. In order to define the Z-score between two terms m and n, Z-score (m, n), several other measures are defined. Let $D_n$ represent the number of text units which contain the term n, and let $F_n^m$ represent the number of those text units in $D_n$ which contain the term m. Then, $P_n^m$, the proportion of co-occurrences of terms m and n to the frequency of term m, can be computed as follows $$P_n^m = \frac{F_n^m}{D_n} \qquad (3)$$

Based on this probability, the mean probability of the term m across all background text units is calculated as follows:

$$\overline{P^m} = \frac{\sum_{i=1}^{U} P_i^m}{U} \qquad (4)$$

where U is the total number of terms that co-occur with the term m. Likewise, the deviation of the term probability distribution, $\sigma^m$, can be computed as follows:

$$\sigma^m = \sqrt{\frac{1}{U-1}\sum_{i=1}^{U}(P_i^m - \overline{P^m})^2} \qquad (5)$$

From equations 3, 4 and 5, Z-score between terms m and n can be calculated as follows:

$$Z\text{-score}(m, n) = \frac{P_n^m - \overline{P^m}}{\sigma^m} \qquad (6)$$

Term Frequency-Inverse Document Frequency (TF-IDF). The TF-IDF is a statistical measure used to evaluate the importance of a word in a document, within a collection of documents. Intuitively, the importance of a term increases as its frequency increases in a document, but the overall frequency of the term in a collection of documents decreases this measure. The TF-IDF has been commonly adopted in practice to measure the correlation between terms in a collection of documents. A similar method can be used to compute the association between a pair of terms m and n based on the following:

$$TF\text{-}IDF_n^m = TF_n^m \times IDF_n = t_n^m \times \log\left(\frac{N}{t_n}\right) \qquad (7)$$

where $t_n^m$ is the number of text units that contain both m and n, $t_n$ is the number of text units that contain n, and N is the total number of text units.

Finding Indirect Associations

The direction association above provides a way to connect the concepts within a corpus to find indirect associations. In this way, the concepts can be represented by a graph, in which a 'node' corresponds to a 'concept', and an edge between two nodes represents the association between the corresponding concepts. The edges have a 'weight' property, which is equal to the 'association' measure of the corresponding concepts to the source and target nodes.

Figure 2:
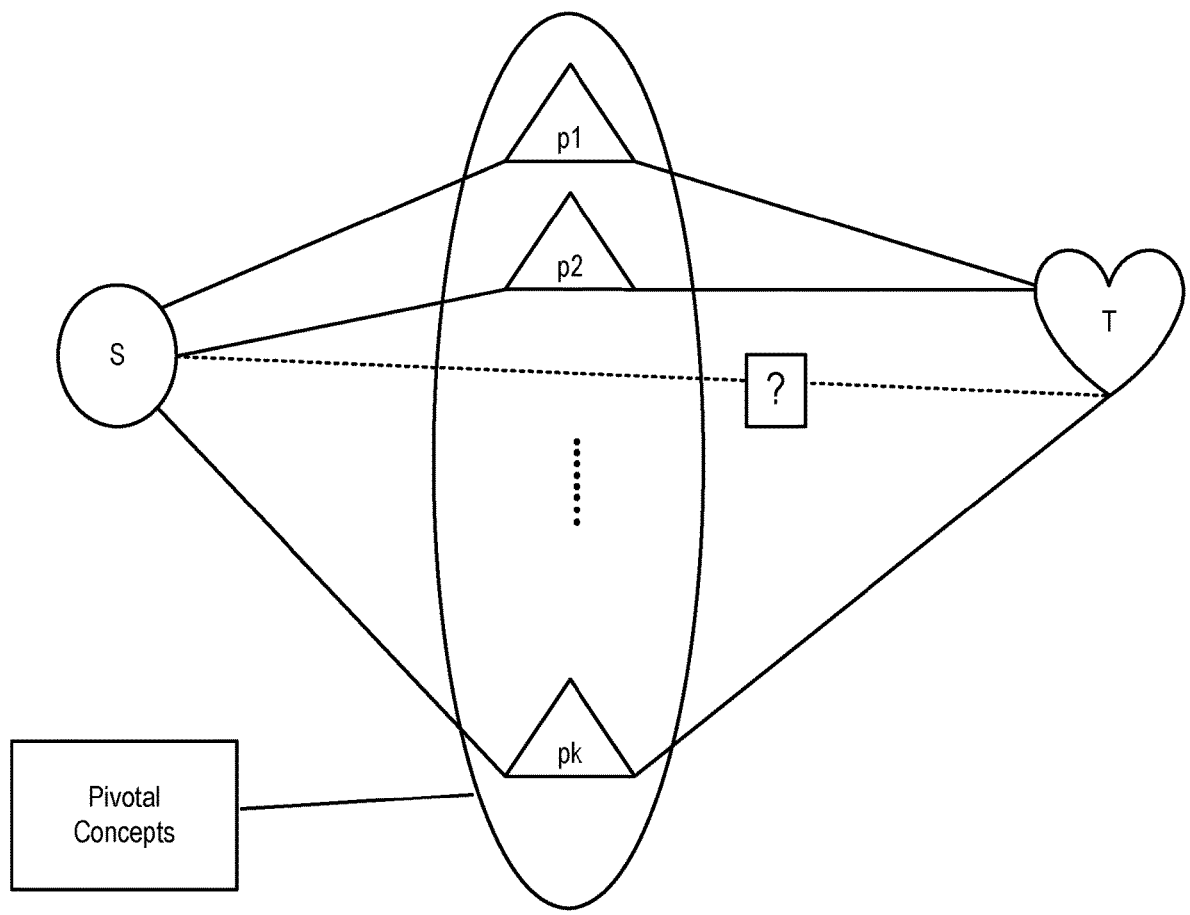
FIG. 2 illustrates a general scheme for establishing a hypothesis for indirect associations from direct association, the general scheme having one or more features consistent with the present disclosure.

Representing the concepts and their 'direct' associations as a graph, helps establish an hypothesis regarding a pair of nodes, which are not connected directly, but are likely to be associated through a group of intermediate 'linking' concepts to which both concepts are connected. One general scheme for establishing a hypothesis for indirect associations from direct associations is shown in FIG. 2. For a pair of source and target concepts S and T, the indirect associations is evaluated based on the links connecting these two concepts through pivotal concepts $p_i$.

The indirect associations are computed between a pair of source and target concept, using a method known as Average Minimum Weight (AMW), which is based on computing the indirect association score between the source concept S and the target concept T using the amount of information between the source concept and each of the linking (pivotal) concepts $L_i$, and also the amount of information between the linking concept $L_i$ and the target concept. More formally, $$Score(S, T) = \frac{\sum_{i=1}^{n} \min(DS(S, L_i), DS(L_i, T))}{n} \qquad (8)$$

where $L_i$ is the ith linking concept, DS is the direct association score between two concepts (computed by one of the measures presented in Section 3.1), and n is the number of linking concepts. The intuition behind using the min function is that the amount of information inferred between a pair of source and target concept through a linking concept would be no greater than the least information between the source and linking concept, and that of the linking concept and target concept.

Scalability and Implementation Issues

To make computation of associations scalable, a linear scan of the dictionary can be done, and for each term in the dictionary query the search engine for all the occurrences of that term in text units of interest (in some implementations, a window of length 10 words is used). In the second step, and to find the concepts associated with a given query word q, the direct associations are calculated (using one of the measures presented above) between q and the concepts in the dictionary which are appeared at least once in a text unit around q. This results in a huge reduction in unnecessary pair-wise association evaluation between concepts that cannot be associated. As a result, the associated concepts with q can be found in constant time. This is significant speed-up compared to pair-wise association calculations. In some implementations, the indexing and query processing engine can use Elasticsearch, which is a search server based on Lucene, and provides scalable search, has near real-time search, and supports multitenancy.

Experimental Evaluation

Two datasets were used to evaluate the performance and utility of proposed techniques. The first dataset contains 1000 pairs of gene-disease associations selected randomly from the DisGeNET database. The DisGeNET database integrates human gene-disease associations (GDAs) from various expert curated databases and text-mining derived associations including Mendelian, complex and environmental diseases. The second dataset contains 12 diseases along with their symptoms and prescriptions drugs, which have been collected manually from medicinenet.com website.

Gene-Disease Associations

Associations between candidate concepts were computed from the set of all the unique terms among 1000 pairs of known associations (The candidate concepts are selected based on the technique described above). The measure used for computing the associations are PMI and PMIcount measures. In the next step, the association scores are sorted in decreasing order and selected the top 1000 associated concepts.

Figure 3:
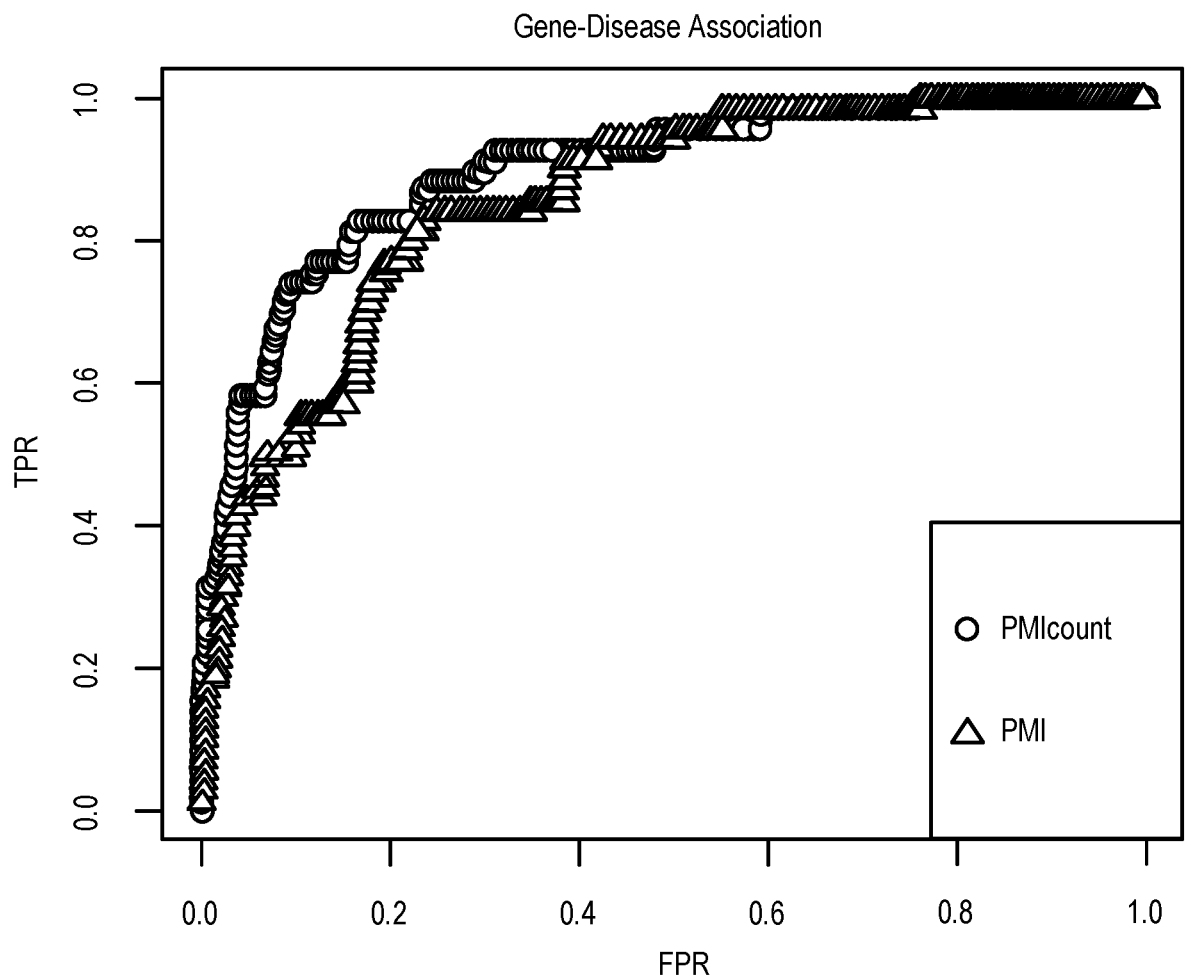
FIG. 3 illustrates a result of comparing pairs of associations found using different measures with true pairs of associations in a dataset.

The top 1000 pairs of associations found are compared using each of the measures with true pairs of associations in the dataset. The result of comparison is shown in FIG. 3. In this figure, the rate of true positives (TPR) is plotted against the rate of the false positives (FPR) for two association measures PMI and PMIcount. As it can be observed, the PMIcount does a better job in computing the scores and finding the pairs which are truly associated in the reference database. For a false positive rate of 15%, the PMIcount can find 80% of true associations.

An online dictionary, such as Wikipedia, can be used as a public source of knowledge, and it has its own limitations in terms of knowledge which can be extracted. For instance, not all the genes in the 1000 pairs of known associations are found in Wikipedia. This basically means that the associations in which these genes are involved cannot be found no matter what association measures are used for analysis. Another example of limitations of the underlying knowledge base is that there is not sufficient information about some associations in Wikipedia. In the absence of such knowledge, the underlying statistical methods cannot find the associations between relevant concepts.

The associations found by methods described herein cannot be thoroughly evaluated based on the reported associations in DisGeNET database. Some associations between genes and diseases which were not documented in the reference database were found, but there is evidence of completed or ongoing research works which support the discovered associations by the methods disclosed herein. Examples of these results are the associations between the deafness gene and corneal dystrophy disease and also the mediterranean fever gene and the amyloidosis disease.

Given the abovementioned limitations, the achieved results could be improved by exploring more comprehensive sources of knowledge or medical databases.

Disease-Symptom-Treatment Associations

As it was mentioned, a group of diseases, and their symptoms and treatments were collected manually. One goal is to evaluate the proposed techniques in finding direct associations and indirect associations based on all the measures presented above. In this experiment, the direct associations between every pairs of concepts which belong to different groups are first computed (i.e. diseases, symptoms, and treatments), after applying pruning techniques discussed above. The reason for selecting pairs in different groups is to focus on associations between diseases and their symptoms and treatments rather than disease-disease or symptom-symptom associations, which could be a separate analysis of interest. For each concept, the top 20 concepts which are found associated with it are selected, to focus on the most significant associations. In the second step, selected pairs of concepts in different groups are selected which are not found associated in the first step, and calculated indirect association score between concepts in selected pairs.

Figure 4:
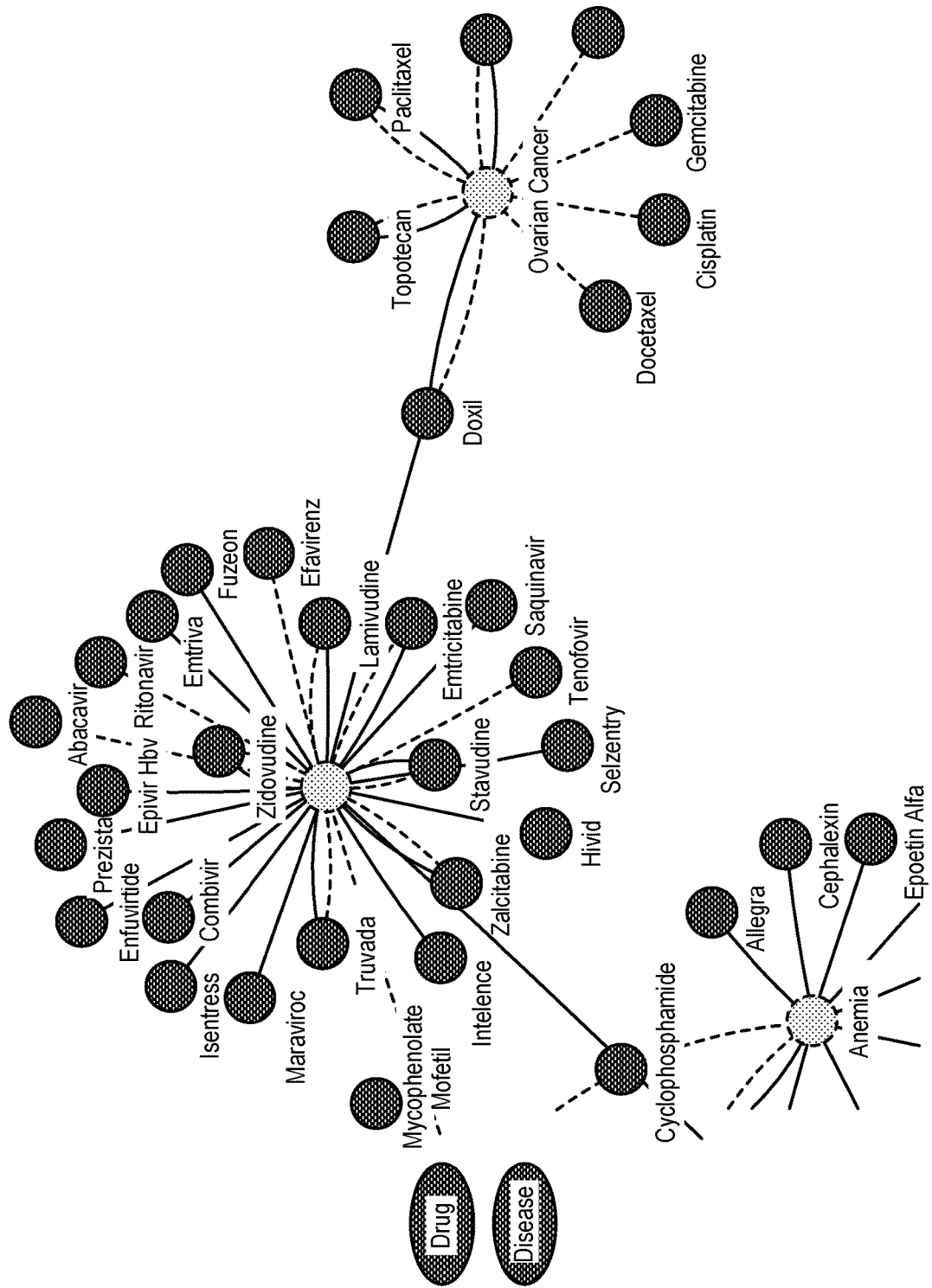
FIG. 4 is a graph in a use case of associating disease with symptoms and drugs for combating disease.

The two-way associations are analyzed between concepts step-by-step, which results in three associations of type 1) disease-symptom, 2) disease-drug, and 3) symptom-drug. The associated pairs are compatible with true associations between diseases, and their symptoms and drugs. FIG. 4 represents part of the graph derived by Neo4J, in which nodes corresponding to diseases are shown in the center, and the nodes corresponding to drugs are shown as extending from the center. The interesting result is that all the drugs associated with the 'HIV' disease are 'true' drugs for this disease in the collected dataset. The association measure used in this graph is based on PMIcount, which performs better than 3 other measures in overall.

In order to compare the rankings provided by different association scores, "Kendall" rank correlation coefficients are computed between measures. The Kendall rank coefficient is a measure of similarity of the orderings of the data when ranked by different methods. The main idea of Kendall rank coefficient is that it compares the number of concordant pairs with the number of discordant pairs. Let X and Y represent the ranks of elements provided by two methods. Any pair of observations $(x_i, y_i)$ and $(x_j, y_j)$ are said to be concordant if the ranks for both elements agree; that is, if both $x_i > x_j$ and $y_i > y_j$ or if both $x_i < xj$ and $y_i < y_j$. They are said to be discordant, if $x_i > x_j$ and $y_i < y_j$ or if $x_i < x_j$ and $y_i > y_j$. If $x_i = xj$ or $y_i = y_j$, the pair is neither concordant nor discordant. The Kendall rank coefficient is defined as follows:

$$\tau = \frac{(C-D)}{\frac{1}{2}n(n-1)} \qquad (9)$$

in which C and D refer to the number of concordant pairs and discordant pairs, respectively, and the denominator is equal to the total number of pairs.

Figure 5:
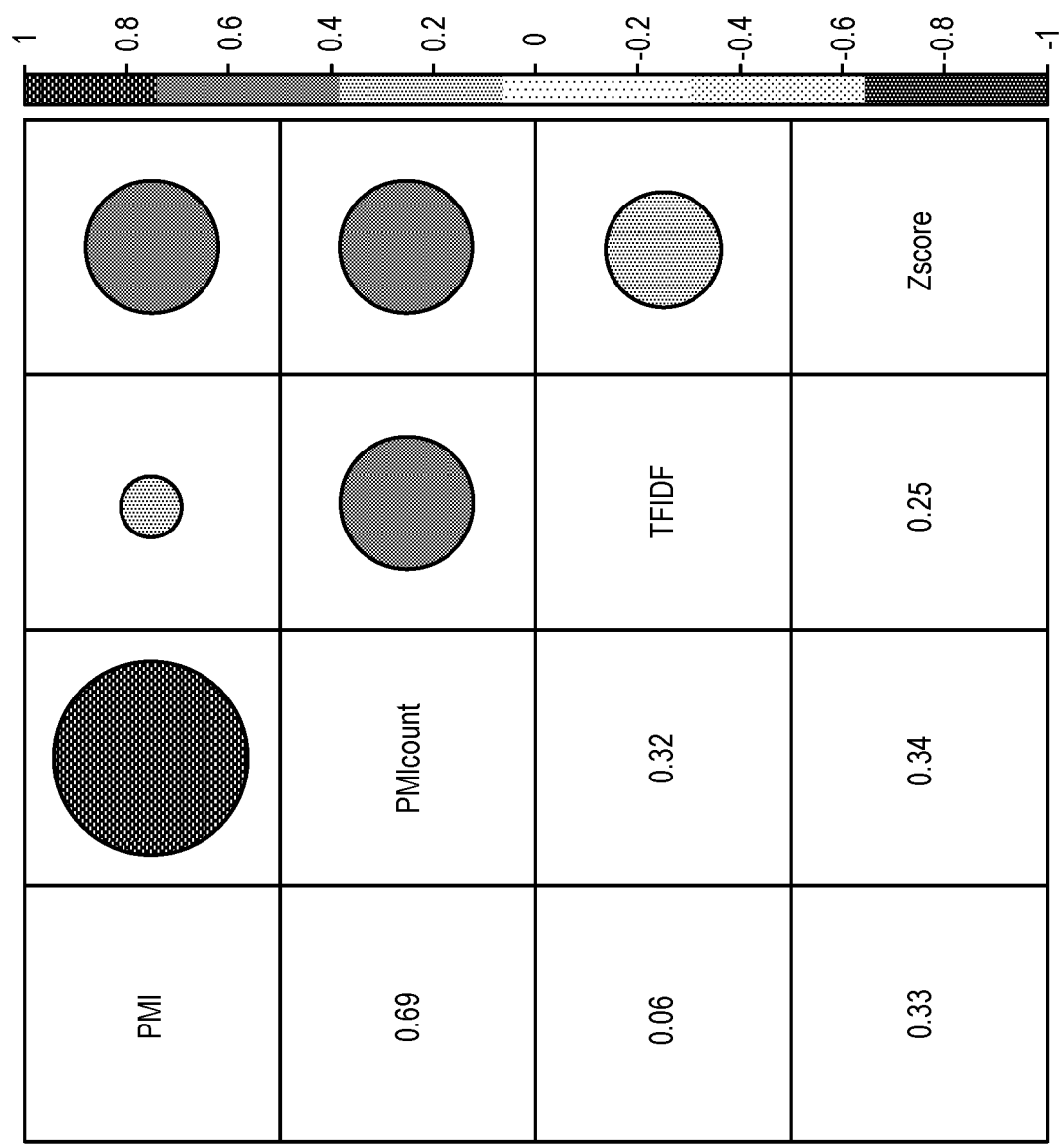
FIG. 5 is an illustration of Kendall rank coefficients between pairs of measures; and, FIGS. 6A-6D are graphs of clustering results of disease-drug associations based on a Z-score, in accordance with implementations described herein.
Figure 6A:
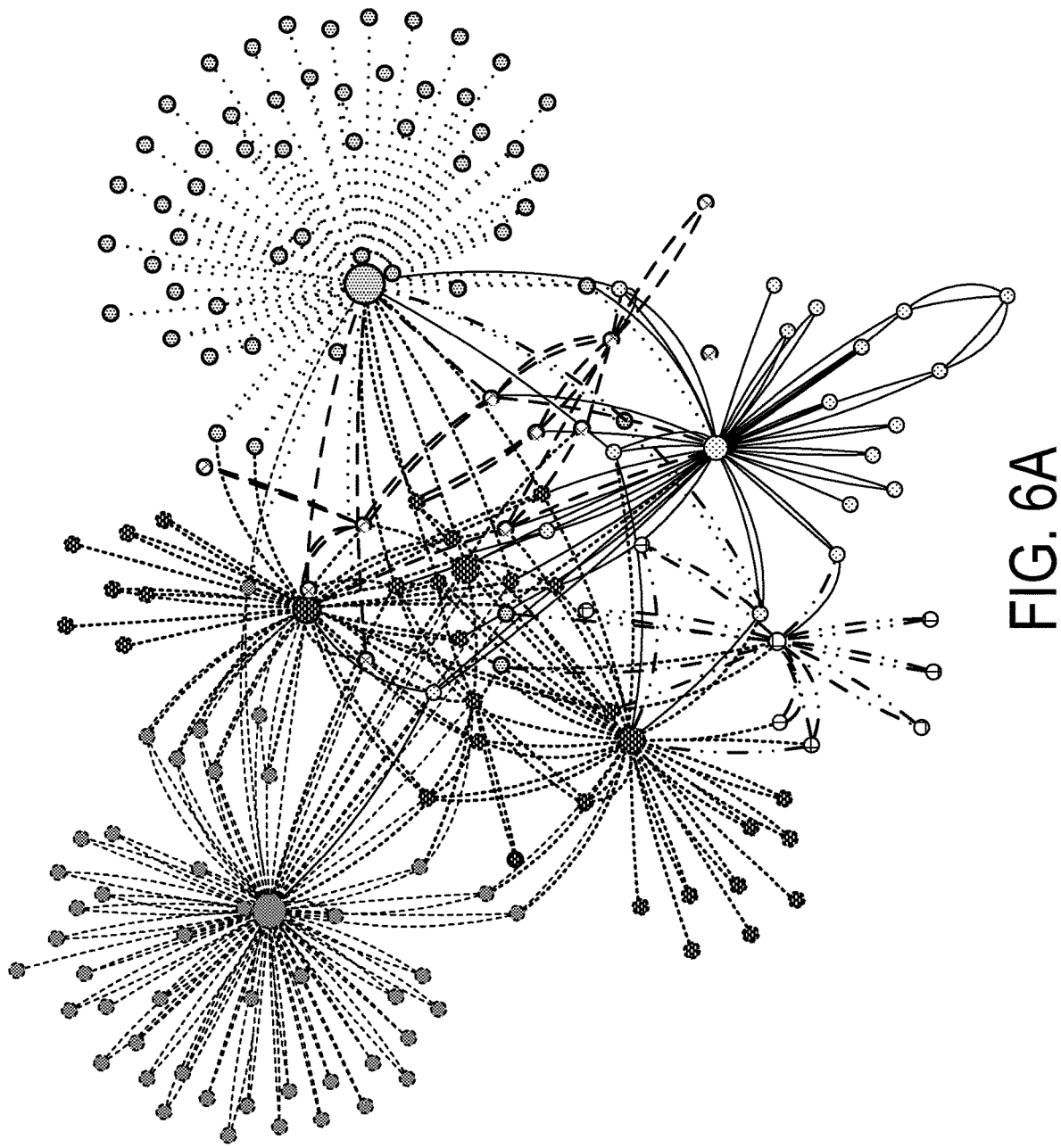
Figure 6B:
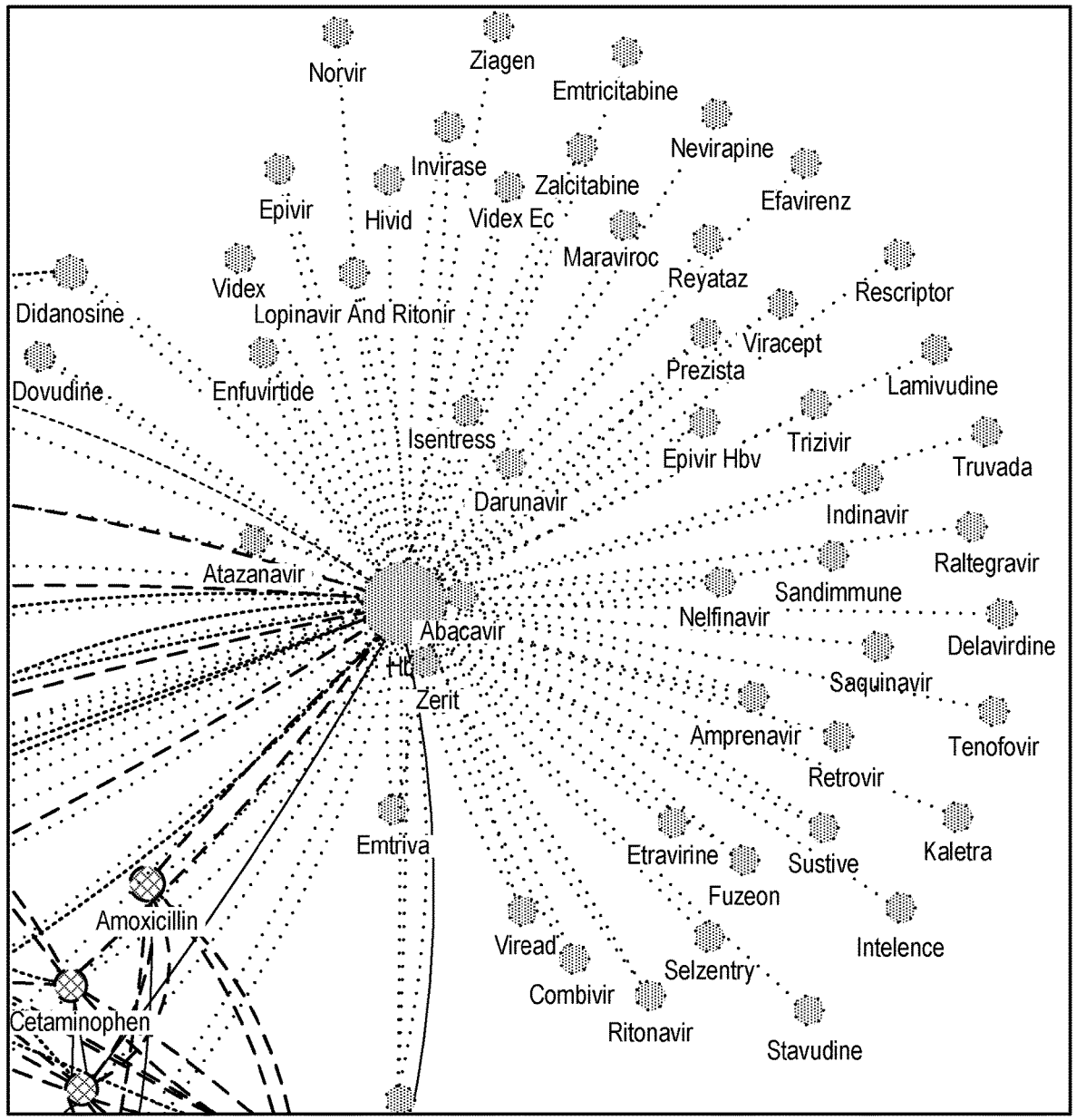
Figure 6C:
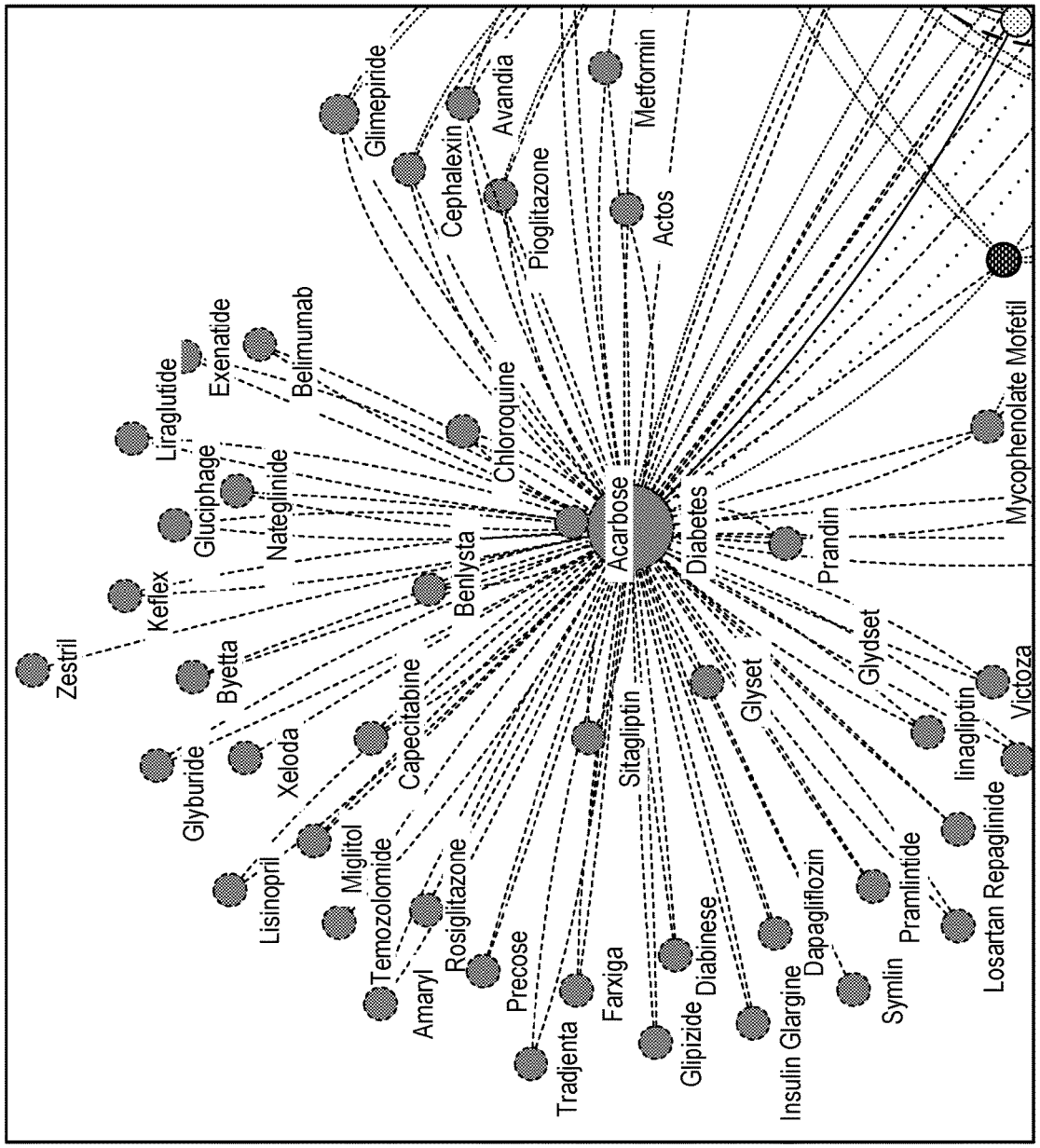
Figure 6D:
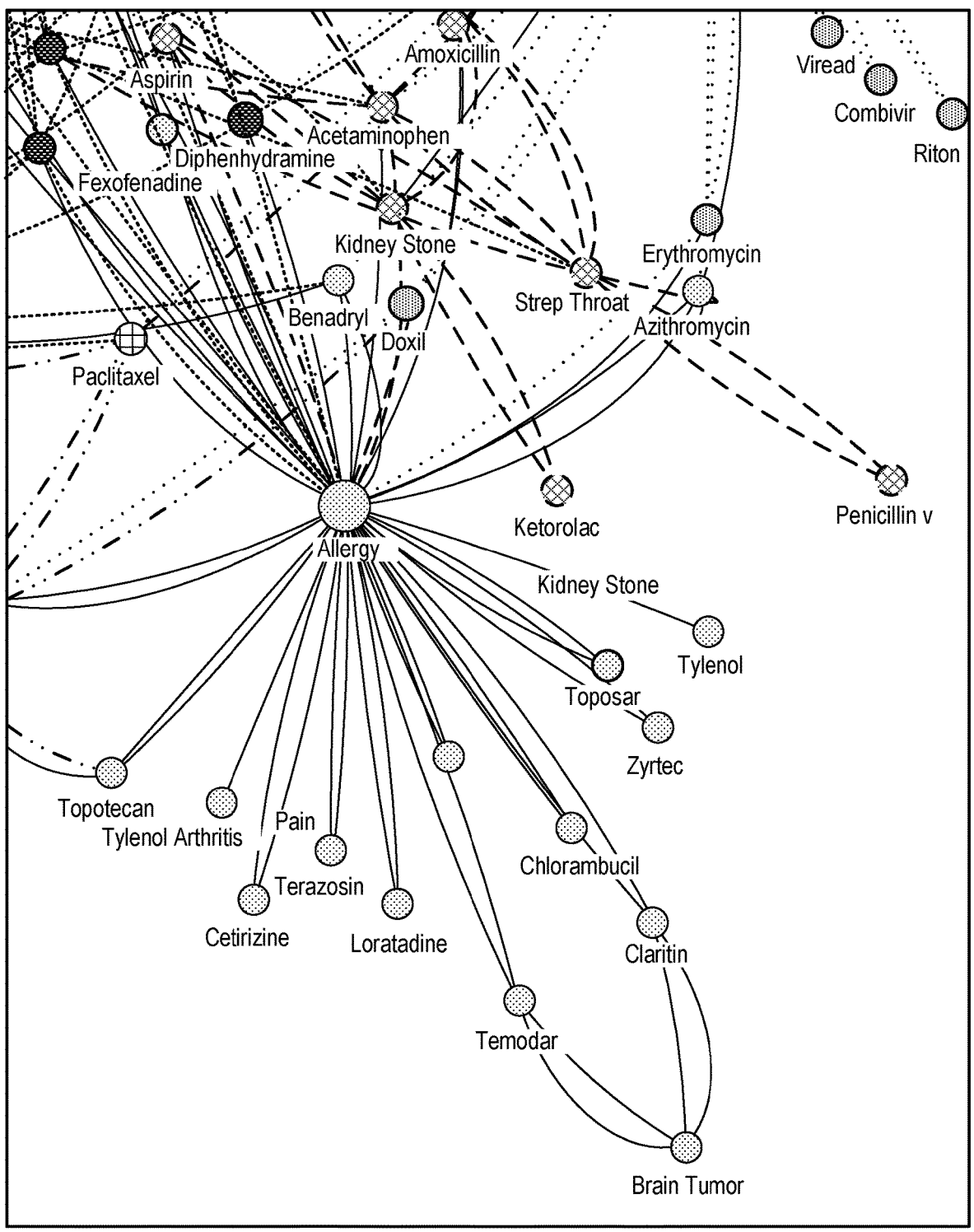

The Kendall rank coefficients between each pairs of measures are shown in FIG. 5. The symmetry in the matrix comes from obvious property of this correlation coefficient. As it is shown in this figure, the PMIcount and PMI have the highest correlation coefficients. This is compatible with similarity of these measures. Moreover, it can be observed from FIG. 5 that PMICount, Z-score, and TF-IDF have similar correlations with each other.

Visualization and Analytics

A visualization tool such as the Neo4J graph database can be used as a visualization layer on top of the extracted associations between concepts. There are several advantages in using Neo4J as an interface layer to users. First, it provides a high-level, user-intuitive summarization of concepts and their associations in which users can easily observe the big picture of relations, and also take advantage of zoom-in features of the visualization layer to focus on a partial subgraph. The edges in a Neo4J graph automatically reflect the distance between concepts, which is the inverse of the association measure computed for the corresponding source and target concepts. Second, the Cypher query language of Neo4J is inspired based on SQL and can be used run ad hoc queries for thorough analysis of a network. This becomes particular handy when dealing with a huge graph representing a large number of concepts. An example query of interest in the disease-symptom-drug case study presented above, is to find the symptoms or drugs common between two diseases. The cypher query to find the drugs common between the "strep throat" and "allergy" is shown in the following:

cypher(graph,
    "MATCH (o: From {name: 'strep throat'})
    <--(w: Weight)
    -->(drug:To)
    <--(w2:Weight)
    -->(o2:From {name: 'allergy'})
    RETURN
    o.name, w.weight, drug.name,
        w2.weight, o2.name")

The result of the above-mentioned query is shown in Table 1, below. In Table 1, the column "o.name" represents the name of the first concept ('step throat'), the column "w.weight" represents the association between the first concept and found drug, the column "drug.name" represent the name of the drug, the column "w2.weight" represents the associations measure between the found drug and the second concept ("allergy"), and the column "o2.name" shows the second concept involved in the association.

TABLE 1

THE RESULTS ON CYPHER QUERY TO RETURN THE DRUGS COMMON BETWEEN "STREP THROAT" AND "ALLERGY"

| o.name | w.weight | drug.name | w2.weight | o2.name |
|---|---|---|---|---|
| strep throat | 0.057 | aspirin | 0.034 | allergy |
| strep throat | 0.158 | corticosteroids | 0.039 | allergy |
| strep throat | 0.149 | acetaminophen | 0.149 | allergy |
| strep throat | 0.129 | azithromycin | 0.129 | allergy |
| strep throat | 0.130 | amoxicillin | 0.043 | allergy |

In addition to query support, the analytics capabilities of the Neo4J graph database can be utilized to get valuable insights about characteristics of a concept graph. Examples of graph analysis include the "betweenness centrality" of nodes, and community detection algorithms. The betweenness centrality of a node V is defined to be the number of shortest paths from all nodes to all others that pass through the node V. The betweenness centrality and its visualization features in Neo4J can highlight some nodes of the graph based on their centrality in some relationship of interest, by incorporating their relative centrality in the diameter of the nodes. Another interesting feature of the Neo4J graph database is its community detection algorithm which can group the nodes of a huge graph into 'clusters' based on their connectedness through the relationship of interest (e.g. an association measure in the presently-described application). Several snapshots of the clustering results of a disease-drug association graph based on Z-score are shown in FIG. 6. The snapshots include all the detected clusters in FIG. 6(a), the clusters around the 'HIV' disease in FIG. 6(b), the clusters around the 'diabetes' disease in FIG. 6(c), and the cluster around the "allergy" disease in FIG. 6(d). It worth mentioning that centrality and relatively larger sizes of the 'disease' nodes in the clusters are the by-product of the betweenness centrality and community detection algorithms employed by the Neo4J. In other words, no extra knowledge is provided to the visualization framework regarding the "size," "centrality" or the types (disease or drug) of the nodes in addition to their association's measures.

Moreover, Neo4j is proved to be efficient in handling large-scale graphs with support for several key scalability features including full data redundancy, service fault tolerance, and linear read scalability. An interesting feature of Neo4J which makes it useful in the presently-described application is that as dataset size increases, the time it takes to get the relationships off any given node stays constant. In contrast, the performance of a relational database is directly tied to the total number of rows in the table being queried. As the number of rows increases, performance degrades, regardless of index use.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT), a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A computer implemented method for determining and representing associations between text-based concepts from unstructured data, the method comprising:
   receiving, by at least one data processor, a request for determining an association between at least two text-based concepts from the unstructured data, the request including a definition of the at least two text-based concepts and a subject domain;
   accessing, by the at least one data processor, one or more data sources of the unstructured data;
   computing, by the at least one data processor, a rank correlation between pairs of the at least two text-based concepts, the rank correlation being computed according to a measure of similarity within the subject domain and generating a Kendall rank coefficient for the pairs of the at least two text-based concepts;
   generating, by the at least one data processor, a graphical representation of the rank correlation between the pairs of the at least two text-based concepts; and
   generating, by the at least one data processor, a rendering of the graphical representation on a graphical display device.

2. The method in accordance with claim 1, further comprising calculating, by the at least one data processor, an indirect association between a second pair of the at least two text-based concepts.

3. The method in accordance with claim 2, further comprising generating, by the at least one data processor, a rendering of a graphical representation of the indirect association on a graphical display device.

4. The method in accordance with claim 1, wherein the rank correlation includes generating a Kendall rank coefficient based on comparing the number of concordant pairs with the number of discordant pairs for the at least two text-based concepts.

5. The method in accordance with claim 1, wherein the graphical representation of the rank correlation between the pairs of the at least two text-based concepts includes a node representing a first concept, and branches representing associated concepts.

6. The method in accordance with claim 1, further comprising calculating, by the at least one data processor using predictive modeling, a target variable based on one or more features extracted from the at least two text-based concepts, the target variable being used to compute the rank correlation.

7. A computer program product comprising a machine-readable medium storing instructions that, when executed by at least one programmable processor, cause the at least one programmable processor to perform operations comprising:
   receiving a request for determining an association between at least two text-based concepts from the unstructured data, the request including a definition of each of the at least two text-based concepts and a subject domain;
   accessing one or more data sources of the unstructured data;
   computing a rank correlation between pairs of the at least two text-based concepts, the rank correlation being computed according to a measure of similarity within the subject domain based on comparing the number of concordant pairs with the number of discordant pairs for the at least two text-based concepts;
   calculating, using predictive modeling, a target variable based on one or more features extracted from the at least two text-based concepts, the target variable being used to compute the rank correlation; and
   generating a graphical representation of the rank correlation between the pairs of the at least two text-based concepts.

8. The computer program product in accordance with claim 7, further comprising calculating, by the at least one data processor, an indirect association between a second pair of the at least two text-based concepts.

9. The computer program product in accordance with claim 8, further comprising generating, by the at least one data processor, a rendering of a graphical representation of the indirect association on a graphical display device.

10. The computer program product in accordance with claim 7, wherein the rank correlation includes generating a Kendall rank coefficient for each of the pair of concepts.

11. The computer program product in accordance with claim 7, wherein the graphical representation of the rank correlation between the pairs of the at least two text-based concepts includes a node representing a first concept, and branches representing associated concepts.

12. The computer program product in accordance with claim 7, further comprising generating a rendering of the graphical representation on a graphical display device.

* * * * *

UNITED STATES PATENT AND TRADEMARK OFFICE
CERTIFICATE OF CORRECTION

Page 1 of 1

PATENT NO. : 10,878,341 B2
APPLICATION NO. : 15/464254
DATED : December 29, 2020
INVENTOR(S) : Reza Sadoddin, Osvaldo A. Driollet and Yanying Chen It is certified that error appears in the above-identified patent and that said Letters Patent is hereby corrected as shown below:

On the Title Page

Item (72), the Inventor information should be changed as follows:
--Inventors: Reza Sadoddin, San Jose, CA (US);
Osvaldo A. Driollet, San Diego, CA (US);
Yanying Chen, San Diego, CA (US)--

Signed and Sealed this
Eleventh Day of October, 2022

Katherine Kelly Vidal
*Director of the United States Patent and Trademark Office*